(12) United States Patent
Klotz et al.

(10) Patent No.: US 6,744,852 B2
(45) Date of Patent: Jun. 1, 2004

(54) ANTI-SCATTER GRID FOR AN X-RAY DEVICE

(75) Inventors: Erhard Paul Artur Klotz, Neumuenster (DE); Reiner Koppe, Hamburg (DE)

(73) Assignee: Koninklijke Philips Electronics N. V., Eindhoven (NL)

(*) Notice: Subject to any disclaimer, the term of this patent is extended or adjusted under 35 U.S.C. 154(b) by 28 days.

(21) Appl. No.: 10/197,757

(22) Filed: Jul. 19, 2002

(65) Prior Publication Data

US 2003/0021379 A1 Jan. 30, 2003

(30) Foreign Application Priority Data

Jul. 28, 2001 (DE) .......................... 101 36 946

(51) Int. Cl.$^7$ ................................. G21K 1/00
(52) U.S. Cl. ........................ 378/154; 378/149
(58) Field of Search ................ 378/154, 155, 378/147, 149; 250/363.04

(56) References Cited

U.S. PATENT DOCUMENTS 6,438,210 B1 * 8/2002 Castleberry ................. 378/154
6,472,667 B1 * 10/2002 Kline et al. ............ 250/370.09

* cited by examiner

*Primary Examiner*—Craig E. Church
*Assistant Examiner*—Jurie Yun

(57) ABSTRACT

The invention relates to an anti-scatter grid for an X-ray device which serves to reduce scattered radiation generated in an object to be examined and includes a plurality of absorber laminations for the absorption of the scattered radiation and a channel medium which is transparent to X-rays and arranged between the absorber laminations. In order to enable notably simple and precise manufacture of such an anti-scatter grid while the primary radiation is attenuated as little as possible and scattered radiation is attenuated as much as possible, in accordance with the invention a non-elastic high-resistance foam, notably a polymethacrylimide high-resistance foam, is used as the channel medium. The invention also relates to a collimator, for example, for a single-photon emitter or a positron emitter, in which a non-elastic high-resistance foam is also used as the channel medium between the laminations.

9 Claims, 3 Drawing Sheets

ANTI-SCATTER GRID FOR AN X-RAY DEVICE

BACKGROUND

The invention relates to an anti-scatter grid for use in an X-ray device in order to reduce scattered radiation produced in an object to be examined, which grid includes a plurality of absorber laminations for the absorption of the scattered radiation and a channel medium which is transparent to X-rays and is arranged between the absorber laminations. The invention also relates to a collimator for a single photon emitter which includes a plurality of laminations in order to form collimator channels and also a channel medium provided between the laminations.

When an object to be examined is irradiated by means of X-rays, not only primary radiation is produced in the object to be examined, for example, a patient, but also scattered radiation so that a "scatter fog" is superposed on the X-ray image. Because of this additional exposure, the contrast of the X-ray image is reduced to an extent which is dependent on the scattered radiation intensity and the signal-to-noise ratio of the detail to be imaged is also degraded.

In order to reduce the scattered radiation, therefore, X-ray devices are provided with an anti-scatter grid which is arranged between the object to be examined and the X-ray detector and which transmits the primary radiation emanating from the focal spot of the X-ray tube but substantially absorbs the scattered radiation from the object to be examined which is incident on the absorber laminations at various angles.

An X-ray device of this kind is known from U.S. Pat. No. 1,164,987. The absorber laminations are usually made of lead which has a small volume in combination with a high absorptivity. The channel medium in the intermediate spaces between the absorber laminations is paper, fiber or aluminum.

SUMMARY OF THE INVENTION

It is an object of the invention to provide an anti-scatter grid in which the scattered radiation is suppressed as much as possible whereas the primary radiation is transmitted as much as possible. Moreover, the manufacture of the anti-scatter grid should be as simple as possible, geometrically accurate and economical. This object is achieved in accordance with the invention by means of an anti-scatter grid of the kind set forth which is characterized in that the channel medium is a non-elastic high-resistance foam.

The invention is based on the recognition of the fact that air would be the ideal channel medium, but also that the absorber laminations must be arranged in a mechanically rigid and positionally accurate manner so as to achieve an as high as possible homogeneity. It has now been found that a non-elastic high-resistance foam is ideal from these points of view. Such a foam has a high transmissivity for the primary radiation because the density is approximately from 15 to 30 times smaller than that of paper. Furthermore, a high mechanical precision can be achieved for the arrangement of the absorber laminations, because the shape of the material is stable and the material can be suitably worked. Moreover, a desired large number of lines, that is, a large number of absorber laminations per unit of length (for example, cm), of the scatter grid can also be achieved. Furthermore, production defects can be repaired during the manufacture, because the absorber laminations and the channel medium are not glued together. Moreover, the channel material is quite inexpensive.

Preferably, a polymethacrylimide high-resistance foam is used as the channel medium, for example, a foam as marketed under the name Rohacel® This material can be simply worked on fast wood or plastic processing machines, for example, by splitting, cutting, grinding or milling. The use of lubricants is permissible. The final shape and the final dimensions can be imparted to the channel elements after the working (after which they are in parallel), for example, by cold pressing. Thermal deformation and bonding or resinification so as to obtain the ultimate shape are also possible. This material thus enables the manufacture of an anti-scatter grid which has substantially the same properties as an anti-scatter grid utilizing air as the channel medium.

The channel medium in a further preferred embodiment comprises individual, preformed channel elements, a channel element being arranged each time between two absorber laminations. The channel elements are thus preformed and subsequently combined with the absorber laminations so as to form the anti-scatter grid, said assembly being realized either by means of an adhesive or, as in a further preferred embodiment, by holding the assembly together by means of a frame.

Alternatively, it is also possible in principle to form individual slits in a large piece of high-resistance foam, for example, by means of a saw, a hot water jet, a laser or a hot wire, and to arrange the absorber laminations subsequently in said slits. The slits may extend in parallel but also conically.

The anti-scatter grid may be constructed as a flat anti-scatter grid in which the absorber laminations are arranged in parallel. However, the anti-scatter grid is preferably constructed as a focused anti-scatter grid in which the absorber laminations are aligned each time along a line which extends through the focal point of the X-ray source. To this end, said preformed channel elements are preferably shaped so as to be conical with a suitable inclination. It may also be arranged that the overall anti-scatter grid is not flat but curved and hence is shaped as a spherical cap, thus enabling even better focusing with respect to the focal point of the X-ray source and hence an even higher homogeneity.

The individual channel elements in a further preferred embodiment are configured in the form of a grid. This means that parts are removed, preferably by sawing (parallel or conically), from the individual, comparatively flat, elongate channel elements, so that the channel element forms a kind of grid or network when viewed from the side (perpendicularly to the direction of the primary radiation). An even better absorption of the scattered radiation can thus be achieved.

The invention also relates to an X-ray device for forming X-ray images of an object to be examined, which device includes an X-ray source, an X-ray detector and an anti-scatter grid which is arranged between the object to be examined and the X-ray detector as described above. An X-ray device of this kind may be a conventional X-ray system, for example, for projection imaging or a C-arm X-ray system, but also a computed tomography system.

The invention also relates to a collimator, notably for a gamma camera of a single photon emitter (SPECT) or for a positron emitter (PET). A non-elastic high-resistance foam can again be advantageously used (for example, in order to save weight) as a channel medium in a collimator of this kind which comprises a plurality of laminations for forming collimator channels and also a channel medium between the laminations. A collimator of this kind is intended notably to transmit only a part of the gamma quanta emanating from the object to be examined to the further elements of a gamma camera which is situated behind the collimator. Only quanta which are incident practically perpendicularly to the surface of the collimator which faces the object to be examined can pass the collimator, whereas quanta which are incident at an angle are absorbed in the collimator walls. In order to achieve an as accurate as possible arrangement of the laminations and to minimize the absorption for the quanta to be transmitted, the described non-elastic high-resistance foam can be used for the channel medium, notably also a polymethacrylimide high-resistance foam such as that marketed under the name Rohacelg. The collimators may then have a linear or grid-like configuration in parallel or focused form. Moreover, the laminations may also be crossed and focused.

Finally, the invention also relates to a gamma camera, a single photon emitter for forming images of a radiating object by means of a gamma camera, the gamma camera being provided with a collimator of the described kind in order to define the projection direction of the image, as well as to a positron emitter.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DETAILED DESCRIPTION

Figure 1:
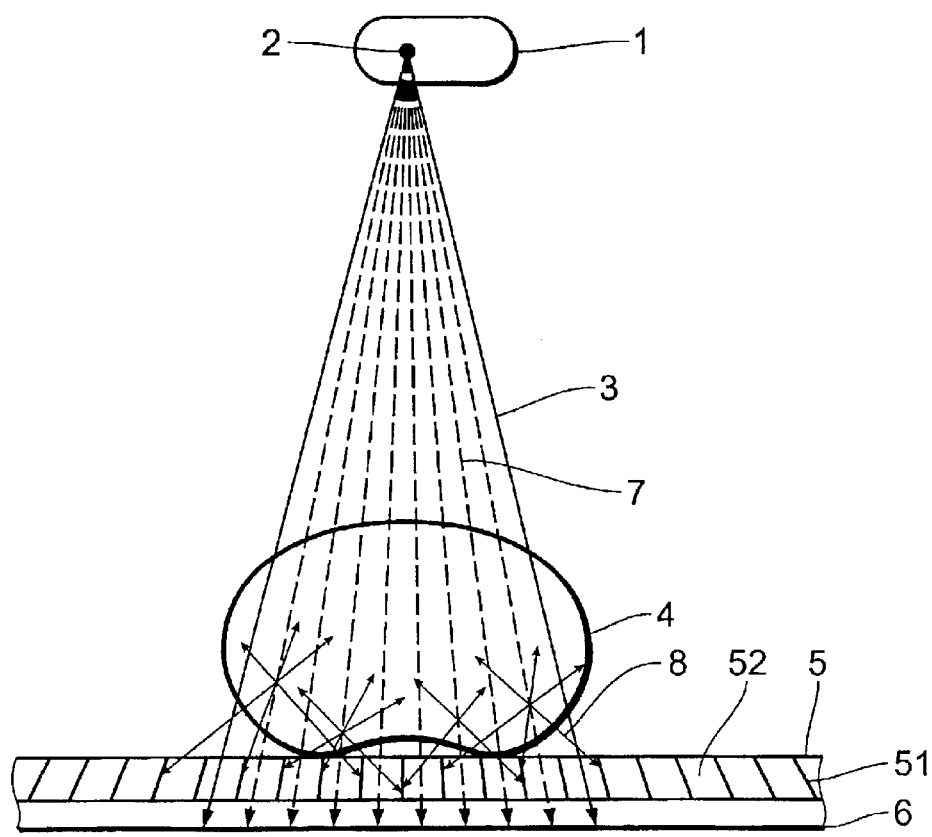
FIG. 1 is a diagrammatic representation of a known X-ray system provided with an anti-scatter grid.

FIG. 1 is a simplified representation of an X-ray system provided with an anti-scatter grid. An X-ray beam 3 is applied from the focal point 2 of the X-ray tube 1 to an object 4 to be examined, for example, a patient. The X-rays traversing the object 4 to be examined are subsequently incident on the anti-scatter grid 5 and the remaining radiation component is ultimately incident on the X-ray detector 6. The anti-scatter grid 5 is composed essentially of absorber laminations 51 and a channel medium 52 which is provided between the absorber laminations 51. The absorber laminations are usually made of lead which has a high absorptivity for X-rays in combination with a small volume, and are directed towards the focal point 2. The channel medium 52 often consists of paper or aluminum and transmits X-rays to the highest possible degree.

The anti-scatter grid 5 serves essentially for transmitting the primary radiation 7 traversing the object 4 to be examined, so that this radiation can be incident on the X-ray detector 6 without any further absorption, whereas scattered radiation 8 produced in the object 4 to be examined should be suppressed as completely as possible so that it cannot be incident on the X-ray detector 6. As is shown in the Figure, the scattered radiation 8 emanates at various angles from the object 4 to be examined and is incident on the absorber laminations 51 in which the scattered radiation 8 is absorbed to a high degree.

Figure 2:
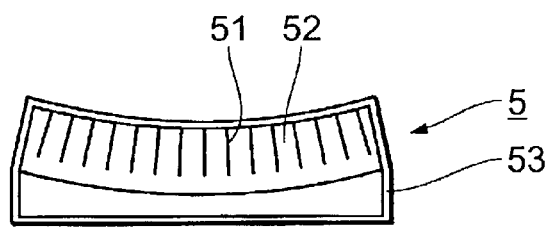
FIG. 2 shows an anti-scatter grid in accordance with the invention.

FIG. 2 shows an anti-scatter grid 5 which is constructed in accordance with the invention. The Figure again shows the absorber laminations 51 with the channel medium 52 arranged therebetween. Moreover, the anti-scatter grid is given a curved shape by means of a suitable frame 53 as shown, so that all absorber laminations 51 are directed towards the focal point or along a straight line which extends through the focal point, that is, perpendicularly to the plane of drawing in FIG. 1. In accordance with the invention, a non-elastic high-resistance foam, notably a polymethacrylimide (PMI) high-resistance foam, for example as marketed under the name Rohacel®, is used as the channel medium 52 in accordance with the invention.

The anti-scatter grid in accordance with the invention is preferably manufactured by providing parallel slits, for example, by sawing or milling, in a non-curved block of high-resistance foam, thin foils which are intended to act as absorber laminations and are made of, for example, lead, tungsten, molybdenum, tantalum, copper or another material which absorbs the X-rays as well as possible are then inserted into said slits.

Because the high-resistance foam is not elastic, the slits can be very accurately formed in exactly specified positions, that is, even in the case of the present small distances and dimensions which are generally in the micrometer range. Subsequently, the curved shape shown in the Figure is imparted to the channel medium 52 and the already inserted absorber laminations 51 by means of the frame 53, said shape being maintained by means of the stable frame 53. The slits may also be cut or milled so as to extend conically.

An anti-scatter grid as shown in FIG. 2 can also be used in a CT system, in which case the frame 53 and the detector are also curved.

Figure 3:
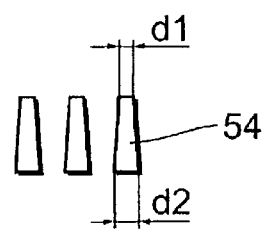
FIG. 3 shows individual channel elements for an anti-scatter grid in accordance with the invention.

In an alternative embodiment of the invention as shown in FIG. 3, individual conical channel elements are made of the high-resistance foam; this can be done very accurately when such a material is used. The absorber laminations are arranged between said channel elements 54 and the assembly is pressed together, resulting in an anti-scatter grid of the kind shown in FIG. 2 which consists of a plurality of channel elements 54 and absorber laminations.

The channel elements 54 and the intermediate absorber laminations 51 can then either be glued to one another or be held together by pressing by means of a frame 53, the latter configuration, however, being preferred. The channel elements 54 in one embodiment have a thickness d1 of, for example, 490 μm at the thin end and a thickness d2 in the range of, for example, 500 μm at the thicker end.

Figure 4:
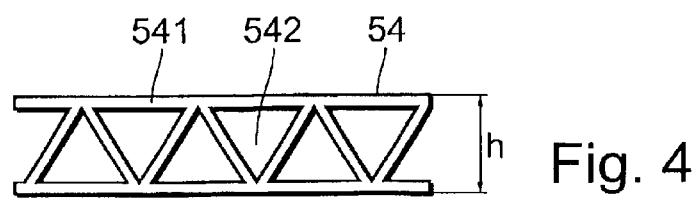
FIG. 4 is a side elevation of a channel element in accordance with the invention.

FIG. 4 is a side elevation of a single channel element 54. Triangular inner regions 542 have been punched from the channel element 54, so that overall only connecting pieces 541 of high-resistance foam remain. It is thus achieved that the absorption of the channel elements 54 for the primary radiation is even further reduced, whereas secondary radiation is absorbed to the same degree. The triangular configuration of the cut-outs 542 as shown has the advantage that a primary beam which is incident on a channel element 54 from above, that is, in the view shown in FIG. 4, and emanates downwards in the plane of drawing has to traverse approximately the same thickness of high-resistance foam material which constitutes the connecting pieces 541. The channel elements in one embodiment have a height h of approximately 40 mm. This type of channel element becomes effective only in the case of large heights.

Figure 5:
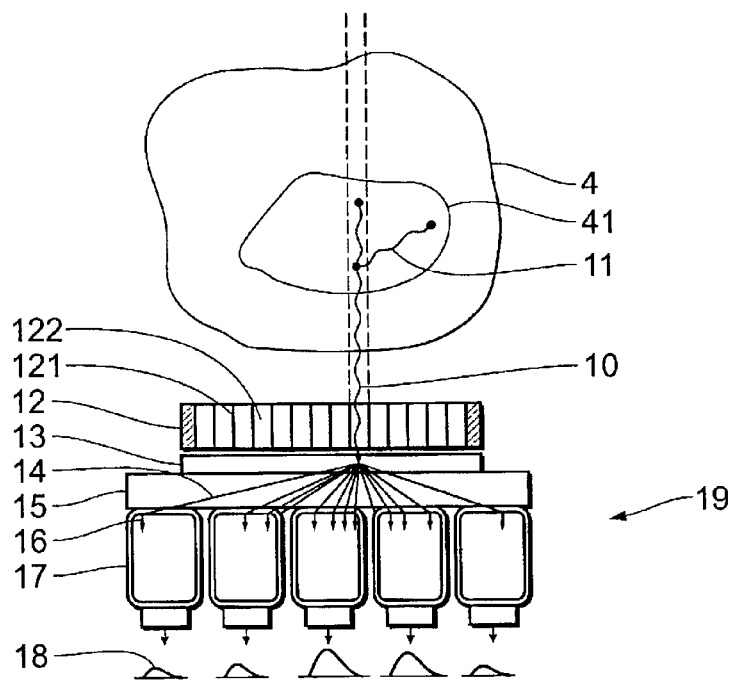
FIG. 5 is a diagrammatic representation of a single photon emitter with a gamma camera.

FIG. 5 shows a circuit diagram of a single photon emitter with a gamma camera. In nuclear medical imaging methods of this kind a metabolic preparation marked by given, unstable nuclides is injected into the patient, said preparation subsequently being enriched in an organ-specific fashion. The detection of the corresponding decay quanta emitted by the body results in an image of the organ, the variation in time of the activity in the organ enabling information to be derived on its functioning.

The SPECT (Single Photon Emission Computed Tomography) method utilizes radio nuclides which decay while emitting a single gamma quantum (γ quantum). In the object 4 to be examined the injected metabolic preparation is enriched in an organ 41 and emits gamma radiation 10, 11, said gamma radiation comprising primary γ quanta 10 and scattered γ quanta 11. Notably the primary γ quanta 10 are then incident on the gamma camera 19. At the entrance of said camera there is provided a collimator 12, for example, a parallel collimator which defines the projection direction of the image. Only quanta which are incident practically perpendicularly to the surface of the collimator can traverse the collimator 12 through the intermediate spaces 122, whereas quanta which are incident at an angle are absorbed in the collimator walls 121 which are formed by laminations. The transmitted quanta are then incident on a monocrystal 13 of NaI(Ti) which absorbs the γ quanta emitted by the object 41. The energy thereof is then converted into a plurality of visible light photons 14 which are conducted to a series of photomultipliers 17 via an optical conductor 15. The electrical output signals 16 of said photomultipliers are used on the one hand for localization, that is, for determining the location of absorption in the crystal 13, and on the other hand for pulse amplitude analysis after summing. FIG. 5 also shows a corresponding output signal 18 of the photomultipliers 17.

It has been found that the non-elastic high-resistance foam material used as the channel medium in anti-scatter grids in accordance with the invention can also be used for the manufacture of collimators for gamma cameras, because such collimators also require a high precision in respect of the distances and alignment of the laminations 121 and because the primary γ quanta 10 should again be absorbed as little as possible before being incident on the crystal 13.

The described high-resistance foam material can thus be used also as the channel medium 122 between the laminations 121, its manufacture being identical or similar to the manufacture described above. The laminations may be made, for example, of lead.

Figures 6A, 6B, 6C:
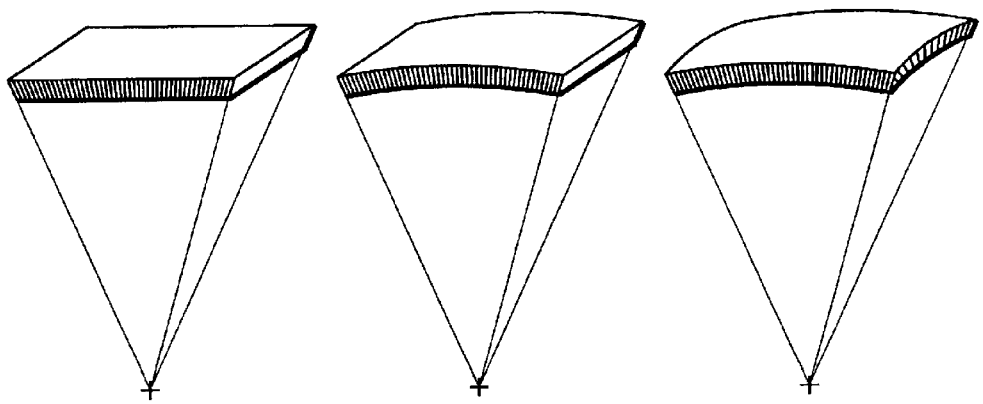
FIG. 6 shows various embodiments of a collimator in accordance with the invention for such a single photon emitter.

The FIGS. 6a,b,c illustrate an example of embodiments of a collimator. FIGS. 6a,b relate to a fan beam collimator with one-dimensionally arranged, focussed laminations. FIG. 6c shows a two-dimensional curved collimator.

In the case of cross grids it is also feasible to use a high-resistance foam of this kind only to form a grid which constitutes the laminations 121 in that a corresponding cross grid is formed in the high-resistance foam (for example, by sawing), the laminations 121 or a hardening metal paste, for example, with lead, being provided in said grid. After hardening, the high-resistance foam material present between the laminations 121 can be removed again so that air is present between the laminations. The cross grid can then be arranged in a flat piece of high-resistance foam. The slits of the grid can extend in parallel or conically. The high-resistance foam section is held together, for example, via a fiber mat provided on the lower surface. After the slits have been provided, the grid is two-dimensionally focused, for example, in a dome-like device. The lamination material is provided in this position as described above.

Figure 7:
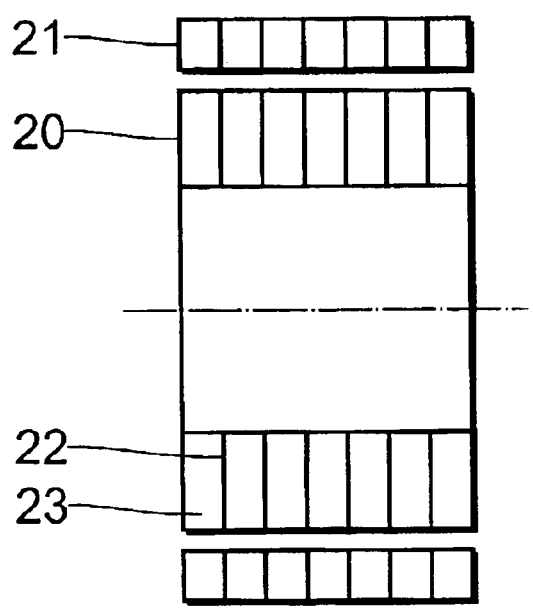
FIG. 7 is a diagrammatic representation of a detector for a positron emitter.

FIG. 7 shows a detector for a positron emitter (PET). The detector 21 is configured as a ring and encloses the collimator 20 which is also configured as a ring. The laminations (septa) 22 are now made of lead foil and the intermediate spaces 23 between the laminations are again filled with the described high-resistance foam. The desired focusing of the γ quanta and the absorption of undesirable quanta can thus be achieved again. The known operation of the positron emitter, however, will not be elucidated herein.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. A grid for use in a radiation device comprising:
   a plurality of absorber laminations for absorbing scattered radiation from a radiation source;
   a channel medium which is transparent to radiation from the radiation source arranged between the absorber laminations, the channel medium comprising a non-elastic, polymethacrylimide high-resistance foam.

2. A grid for use in a radiation device comprising:
   a plurality of absorber laminations which absorb radiation;
   a channel medium being transparent to radiation and arranged between the absorber laminations, the channel medium comprising a non-elastic, high-resistance foam;
   the channel medium is being provided with individual, preformed channel elements, an individual channel element being arranged between the each of the absorber laminations.

3. The grid of claim 2 wherein the channel elements have a conical shape and the channel elements are arranged in such a manner that the prolongations of the absorber laminations intersect one another in a line which extends through a focal point of an x-ray source.

4. The grid of claim 2 wherein the individual channel elements are shaped as a grid.

5. The grid of claim 2 wherein grid is formed by an alternation of channel elements and laminations which are adjacently arranged and held together by a frame.

6. An x-ray device for forming x-ray images of an object to be examined, the x-ray device comprising:
    an x-ray source;
    an x-ray detector, and
    a grid arranged between the object to be examined and the x-ray detector, the grid comprising:
        a plurality of absorber laminations for the absorption of the scattered radiation; and
        a channel medium which is transparent to x-rays arranged between the absorber laminations, the channel medium comprising a non-elastic polymethacrylimide foam.

7. A collimator for a nuclear imaging camera comprising:
    a plurality of laminations for forming collimator channels; and
    a channel medium provided between the laminations, the channel medium comprised of a polymethacrylimide foam.

8. A nuclear imaging camera comprising:
    a radiation detector for producing signals indicative of detected radiation;
    an imaging processor connected to the radiation detector for generating images from the signals indicative of detected radiation; and
    a collimator operatively connected to the radiation detector to define the projection direction of the image of a radiating object, the collimator comprising:
        a plurality of laminations for forming collimator channels;
        a channel medium provided between the laminations, the channel medium comprised of a non-elastic, high-resistance foam; and
        a plurality of individual, preformed channel elements provided in the channel medium, a channel element being arranged between each of the laminations.

9. The nuclear imaging camera of claim 8 wherein the camera is a single photon emission computed tomography camera.

* * * * *